(12) United States Patent
Hulett

(10) Patent No.: US 6,231,553 B1
(45) Date of Patent: May 15, 2001

(54) COLOSTOMY BAG

(75) Inventor: Jeannine Hulett, 4110 NE. 3rd Ave., Pompano Beach, FL (US) 33064

(73) Assignees: Medi-South Products Inc., Pompano Beach, FL (US); Jeannine Hulett, Pompano Beach, FL (US)

( * ) Notice: Subject to any disclaimer, the term of this patent is extended or adjusted under 35 U.S.C. 154(b) by 0 days.

(21) Appl. No.: 09/313,091

(22) Filed: May 17, 1999

(51) Int. Cl.[7] ........................................ A61F 5/44
(52) U.S. Cl. .................. 604/333; 604/332; 604/337; 128/DIG. 24
(58) Field of Search .................. 604/332–345; 128/DIG. 24

(56) References Cited

U.S. PATENT DOCUMENTS

| | | |
|---|---|---|
| 3,507,282 * | 4/1970 | Burding . |
| 4,318,406 | 3/1982 | McLeod . |
| 4,331,148 | 5/1982 | Steer et al. . |
| 4,451,258 | 5/1984 | Jensen . |
| 4,490,145 | 12/1984 | Campbell . |
| 4,542,097 | 9/1985 | Van Polen . |
| 4,620,999 | 11/1986 | Holmes . |
| 4,737,661 | 4/1988 | Marut . |
| 4,911,699 * | 3/1990 | Fenton ................................. 604/333 |
| 5,370,638 | 12/1994 | Keyes . |
| 5,531,724 | 7/1996 | Young et al. . |
| 5,582,820 | 12/1996 | Yamamoto et al. . |
| 5,653,705 * | 8/1997 | De La Torre et al. ................... 606/1 |

* cited by examiner

Primary Examiner—Anhtuan T. Nguyen
Assistant Examiner—Michael M. Thompson
(74) Attorney, Agent, or Firm—Kenneth Tolar

(57) ABSTRACT

A colostomy bag includes a bag member having top and bottom ends, each end having an opening. The opening at the bottom end is sealable with a sliding tab zip-lock type closure means allowing the bag to be easily drained and reused. Mounted to the exterior of the bag member is a pouch having an auxiliary colostomy bag received therein for use in the event that the reuseable bag suddenly ruptures or begins leaking. Also attached to the exterior surface of the bag is a deodorizing means that emits a pleasant odor upon the bag member being moved or shifted.

5 Claims, 1 Drawing Sheet

1

COLOSTOMY BAG

BACKGROUND OF THE INVENTION

The present invention relates to a colostomy bag having a quick release type closure means, allowing the bag to be quickly and conveniently emptied, as well as an emergency bag storage and a deodorizing means.

DESCRIPTION OF THE PRIOR ART

A colostomy is a surgical procedure in which a patient's colon is provided with an artificial opening, referred to as a stoma, through which the colon may be artificially evacuated. A disposable colostomy bag is coupled with the stoma to receive the contents from the colon. The bag is typically constructed with plastic, rubber or a similar liquid impermeable material and has an opening thereon for receiving the stoma. Once the bag is full, it is usually detached from the stoma, discarded, and replaced. The frequent removal and replacement is burdensome, inconvenient, and often irritating to the patient. Accordingly, there is currently a need for a colostomy bag which may be periodically emptied and reused, eliminating the need for frequent replacement.

Although at least one reuseable colostomy bag exists in the prior art, the frequent reuse of the bag makes it susceptible to wear, puncturing or tears. In such event, there is a need for an emergency or replacement bag to minimize spillage.

Finally, the odors associated with the use of colostomy bags can be aggravating and embarrassing. The present invention satisfies the above described needs by providing a colostomy bag having a quick release closure means at a bottom end allowing the bag to be quickly and conveniently emptied and resealed. Furthermore, the device includes a pocket on its exterior surface with an auxiliary colostomy bag therein which may be used in the event of an emergency. Furthermore, the present invention includes a scent producing patch on the exterior surface of the bag which emits a pleasant odor upon movement of the bag.

Various colostomy bag constructions exist in the prior art. For example, U.S. Pat. No. 3,507,282 issued to Burding relates to a colostomy bag having an opening that is resealable with VELCRO® or an adhesive, such as pressure sensitive tape.

U.S. Pat. No. 4,738,661 issued to Marut relates to a gastronomy belt for use on patients who have undergone a gastronomy surgery.

U.S. Pat. No. 4,620,999 issued to Holmes relates to a system for assuring degradation of body waste bags.

U.S. Pat. No. 4,543,097 issued to Van Polen relates to an ostomy bag. The device includes a non-irritating cloth cover that substantially encloses an ostomy bag and in which a pocket is formed by at least one fold in the cover to receive a deodorizing member. The deodorizing member is impregnated with a volatile deodorant that is warmed and vaporized by a patient's body heat.

U.S. Pat. No. 4,490,145 issued to Campbell relates to an ostomy pouch having a filter element affixed to the pouch outer wall. The filter element includes a polymeric film cover and an insert of gas deodorizing material.

U.S. Pat. No. 4,451,258 issued to Jensen relates to an ostomy bag with an adjustable vent having a deodorizing filter housed therewithin. The air flow through the vent may be varied to enhance the effectiveness of the filter. The vent also permits precise control of the degree of inflation of the bag.

U.S. Pat. No. 4,331,148 issued to Steer et al relates to a deodorizing bag which encloses an ostomy bag. The cover bag is formed of material containing activated carbon or has an area of its inner wall filled with such filtering material.

As indicated above, at least one reuseable colostomy bag and various deodorizing devices for conventional colostomy bags exist in the prior art. Although the reusable bag in Burding includes a resealable opening for periodically emptying the bag, the opening is resealed with an adhesive or VELCRO™. Such a closure means has several disadvantages. The useful life of adhesives is typically limited since they deteriorate with frequent use. Accordingly, the bag is susceptible to sudden leakage or failure. Hook and loop fasteners (VELCRO™) often provide a tenuous, liquid permeable seal and are sometimes cumbersome to join and separate. The present invention relates to a reusable colostomy bag having a sliding tab "ziplock" resealable opening that is durable, long lasting and provides a reliable liquid impermeable seal. The bag also includes a deodorizing means that is automatically activated upon movement of the bag and an emergency bag mounted to the bag exterior in the event that the primary bag suddenly becomes unusable.

SUMMARY OF THE INVENTION

The present invention relates to a reuseable colostomy bag having a resealable opening, a deodorizing means, and an auxiliary bag for emergencies. The device comprises a hollow primary bag member, formed with a liquid impermeable material, having a top end and a bottom end. At the top end is an opening configured and dimensioned to receive a patient's stoma. The bottom end includes a pair of free edges that define a lower opening through which the contents of the bag may be emptied. A first edge includes an elongated strip having a tongue disposed thereon while the opposing edge includes a similar strip having a mating groove thereon forming a "ziplock" type resealable closure means. A tab slidably engages both free edges for selectively joining or separating the mating strips. On the exterior surface of the bag member is a pouch having an auxiliary colostomy bag received therein. A scent producing patch is also mounted on the bag exterior and includes cologne or a similar deodorizing material impregnated on its upper surface which is released upon frictional engagement with an object. Superimposed on the scent producing patch is an activating patch having a coarse lower surface that frictionally engages the upper surface of the scent producing patch. Therefore, upon movement of the bag, the deodorizing material is released to the atmosphere. It is therefore an object of the present invention to provide a colostomy bag having a resealable bottom opening allowing the bag to be emptied and reused.

It is another object of the present invention to provide a colostomy bag having an emergency auxiliary bag secured thereto.

It is yet another object of the present invention to provide a colostomy bag having a deodorizing means thereon.

Other objects, features and advantages of the present invention will become readily apparent from the following detailed description of the preferred embodiment when considered with the attached drawings and the appended claims.

DESCRIPTION OF THE PREFERRED EMBODIMENT

Figure 1:
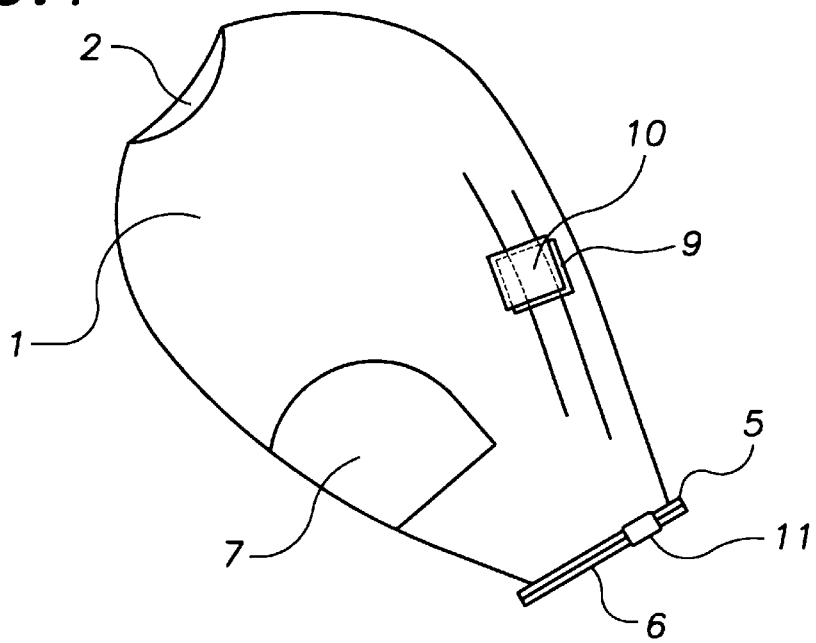
FIG. 1 is a perspective view of the inventive device.
Figure 2:
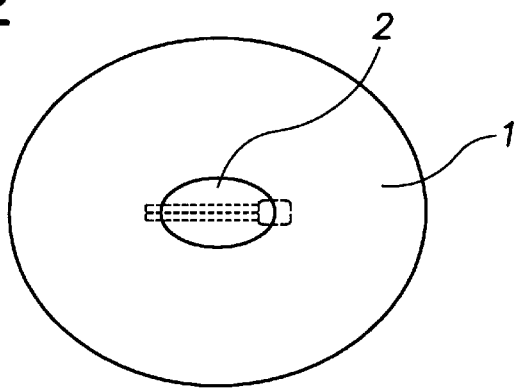
FIG. 2 is a top view of the inventive device.
Figure 3:
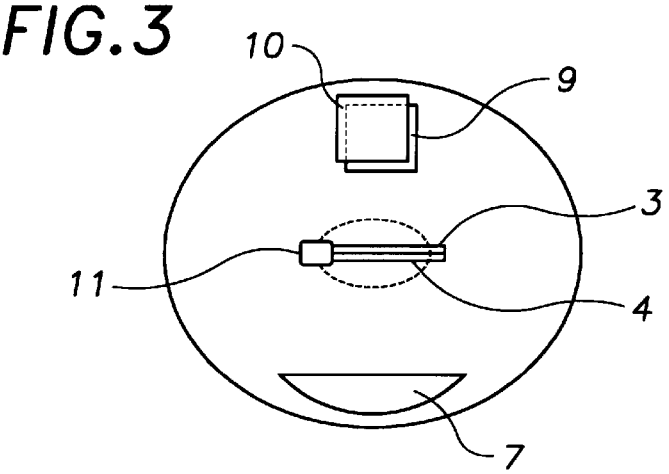
FIG. 3 is a bottom view of the inventive device.

Referring now to FIGS. 1 through 3, the present invention relates to a colostomy bag having a resealable opening allowing the bag to be emptied and reused. The device comprises a primary bag member 1 having a top end, a bottom end, an exterior surface and an interior chamber for receiving waste products via a stoma.

The top end of the bag member includes an opening 2 dimensioned and configured to receive the stoma. The bottom end includes first 3 and second 4 free edges that define a drain opening through which the contents of the interior chamber may be emptied. The drain opening may be selectively sealed with a resealable closure means. The resealable closure means relates to what is commonly referred to as a "zip-lock" type seal and includes a first strip 5 disposed along the entire length of the first free edge of the bag member, the strip having an elongated tongue thereon. A second strip 6 is disposed on the second free edge and includes an elongated groove for matably receiving the tongue. A tab 11 slidably engages both free edges that closes or opens the drain opening. When the tab is slid in a first direction, the mating strips are sealed together. When the tab is slid in an opposite direction, the sealed strips are separated. The resealable closure means may be opened and sealed with infinite frequency without jeopardizing the integrity of the seal. Furthermore, the seal is liquid impermeable thereby preventing leakage.

On the exterior surface of the bag member is a pouch 7 received within which is an auxiliary colostomy bag (not pictured). The auxiliary bag may be a colostomy bag according to the present invention or any conventional colostomy bag. The auxiliary bag functions as an emergency bag in the event that the reuseable bag is punctured or is otherwise unexpectedly damaged.

The colostomy bag according to the present invention also includes a deodorizing means for minimizing the unpleasant odors associated with the use of a colostomy bag. Attached to the exterior surface of the bag member is a substantially rectangular or square patch 9. The upper surface of the patch is impregnated with a scent producing material. The scent producing patch automatically releases the scent producing material upon an object frictionally engaging the upper surface thereof. The scent producing material may be a cologne, deodorant or similar material that emits a pleasant fragrance. Superimposed on the scent producing patch is an activation patch 10 having a coarse lower surface that frictionally engages the upper surface of the scent producing patch. The activation patch is attached to the scent producing patch using any conventional attachment means. Accordingly, upon slight movement of the bag, such as when the patient shifts, a pleasant odor will be automatically emitted to the surrounding atmosphere.

The bag member according to the present invention is preferably constructed with plastic or a similar reuseable, liquid impermeable material. The coarse surface of the activation patch may relate to sandpaper, Emery Board or a similar type material. However, as will be readily apparent to those skilled in the art, the size, shape, and materials of construction of the various components may be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A colostomy bag comprising:

a hollow bag member having an exterior surface, a top opening for receiving a stoma and a bottom opening for draining the contents of said bag member;

a resealable closure means for selectively sealing said bottom opening;

a pouch member attached to the exterior surface of said bag member having an auxiliary bag member received therein.

2. A colostomy bag comprising:

a bag member having an open top end for receiving a patient's stoma, an exterior surface, an interior chamber for receiving waste from the stoma, and a bottom end, said bottom end including first and second free edges defining a second opening through which contents within the interior chamber are drained;

a first strip having a tongue thereon, said strip disposed adjacent the first free edge of said bag member;

a second elongated strip disposed adjacent the second free edge of said bag member, said second strip having a groove thereon for selectively receiving said tongue;

a pouch member mounted to the exterior surface of said bag member, said pouch member having an auxiliary disposable bag member received therein.

3. The colostomy bag according to claim 2 further comprising:

a tab slidably engaging the first and second free edges of said bag member that, when slid in a first direction, joins said first and second strips and when slid in a second direction separates said strips.

4. The colostomy bag according to claim 2 firther comprising: deodorizing means mounted to the exterior surface of said bag member.

5. The colostomy bag according to claim 4 wherein said deodorizing means comprises:

a patch mounted to the exterior surface of said bag member, said patch having an upper surface with a scent producing material impregnated thereon, said scent producing material released to the atmosphere upon the upper surface of said scent producing patch frictionally engaging an object;

an activation patch having a coarse lower surface, said activation patch superimposed on said scent producing patch with said coarse lower surface engaging the upper surface of said scent producing patch whereby said scent producing material is released upon movement of the bag member.

\* \* \* \* \*